United States Patent
Desjardin et al.

(10) Patent No.: US 11,540,859 B2
(45) Date of Patent: Jan. 3, 2023

(54) SURGICAL ACCESS SYSTEM INCLUDING INSTRUMENT RETAINING CLIP

(71) Applicant: Covidien LP, Mansfield, MA (US)

(72) Inventors: Kevin Desjardin, Cheshire, CT (US); Astley C. Lobo, West Haven, CT (US); Christopher A. Tokarz, Torrington, CT (US); Oksana Buyda, East Haven, CT (US); Douglas M. Pattison, East Hartford, CT (US); Alexander Y. Ueno, Hamden, CT (US); Amanda M. Adinolfi, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 315 days.

(21) Appl. No.: 16/784,676

(22) Filed: Feb. 7, 2020

(65) Prior Publication Data

US 2021/0244438 A1 Aug. 12, 2021

(51) Int. Cl.
*A61B 17/34* (2006.01)

(52) U.S. Cl.
CPC .. *A61B 17/3423* (2013.01); *A61B 2017/3445* (2013.01); *A61B 2017/3456* (2013.01)

(58) Field of Classification Search
CPC ............ A61B 17/3421; A61B 17/3423; A61B 2017/3445; A61B 50/22
See application file for complete search history.

(56) References Cited

U.S. PATENT DOCUMENTS

| | | |
|---|---|---|
| 4,707,906 A | 11/1987 | Posey |
| 4,711,636 A | 12/1987 | Bierman |
| 5,290,259 A | 3/1994 | Fischer |
| 5,833,667 A | 11/1998 | Bierman |
| 6,074,368 A | 6/2000 | Wright |
| 6,610,033 B1 | 8/2003 | Melanson et al. |
| 6,936,033 B2 | 8/2005 | McIntosh et al. |
| 7,678,083 B2 | 3/2010 | Stephens |
| 7,785,312 B2 | 8/2010 | Thorne, Jr. et al. |
| 7,918,828 B2 | 4/2011 | Lundgaard et al. |
| 2005/0067308 A1 | 3/2005 | Thompson et al. |

(Continued)

FOREIGN PATENT DOCUMENTS

| | | |
|---|---|---|
| DE | 8627160 U1 | 11/1986 |
| DE | 9417660 U1 | 1/1995 |

(Continued)

OTHER PUBLICATIONS

Extended European Search Report dated Jun. 23, 2021 issued in corresponding EP Appln. No. 21155459.7.

*Primary Examiner* — Si Ming Ku
(74) *Attorney, Agent, or Firm* — Carter, DeLuca & Farrell LLP

(57) ABSTRACT

A surgical access system includes a clip, a cannula, and an obturator. The clip includes a first housing half and a second housing half. The first and second housing halves have first end portions pivotably coupled together and second end portions having respective first and second fastener portions. The clip is movable between an open position in which the second end portions are spaced apart from each other and a closed position in which the first and second fastener portions of the second end portions are engaged with each other. The cannula and the obturator are retained between the first and second housing halves when the clip is in the closed position.

20 Claims, 2 Drawing Sheets

(56) References Cited

U.S. PATENT DOCUMENTS

| | | | |
|---|---|---|---|
| 2005/0228224 A1 | 10/2005 | Okada et al. | |
| 2010/0010449 A1* | 1/2010 | Leibowitz | A61B 17/3421 604/179 |
| 2012/0071740 A1* | 3/2012 | Kaestle | A61B 5/6826 600/323 |
| 2015/0351844 A1* | 12/2015 | Smith | F16B 2/22 24/531 |

FOREIGN PATENT DOCUMENTS

| | | |
|---|---|---|
| EP | 0790063 A1 * | 2/1997 |
| EP | 0790063 B1 | 10/2002 |

* cited by examiner

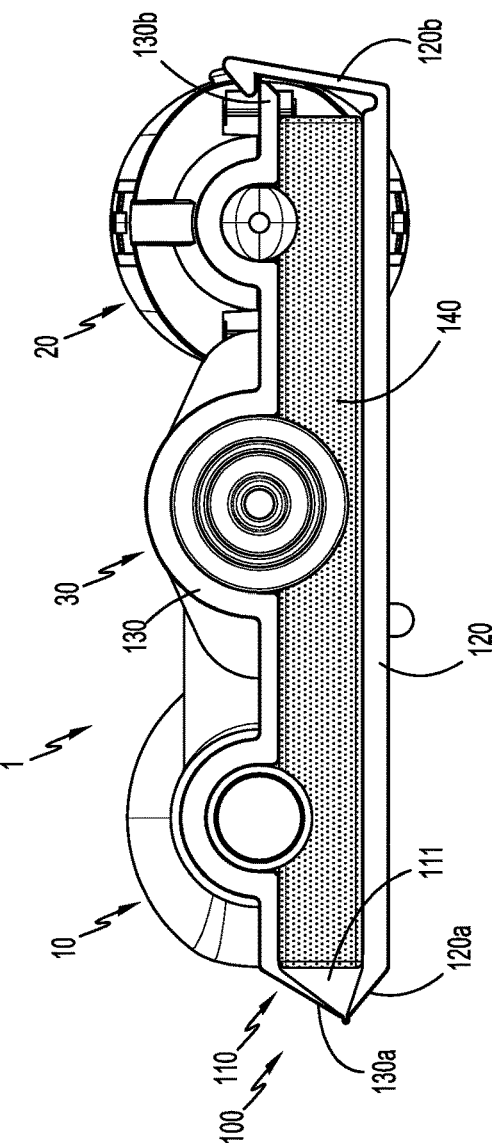
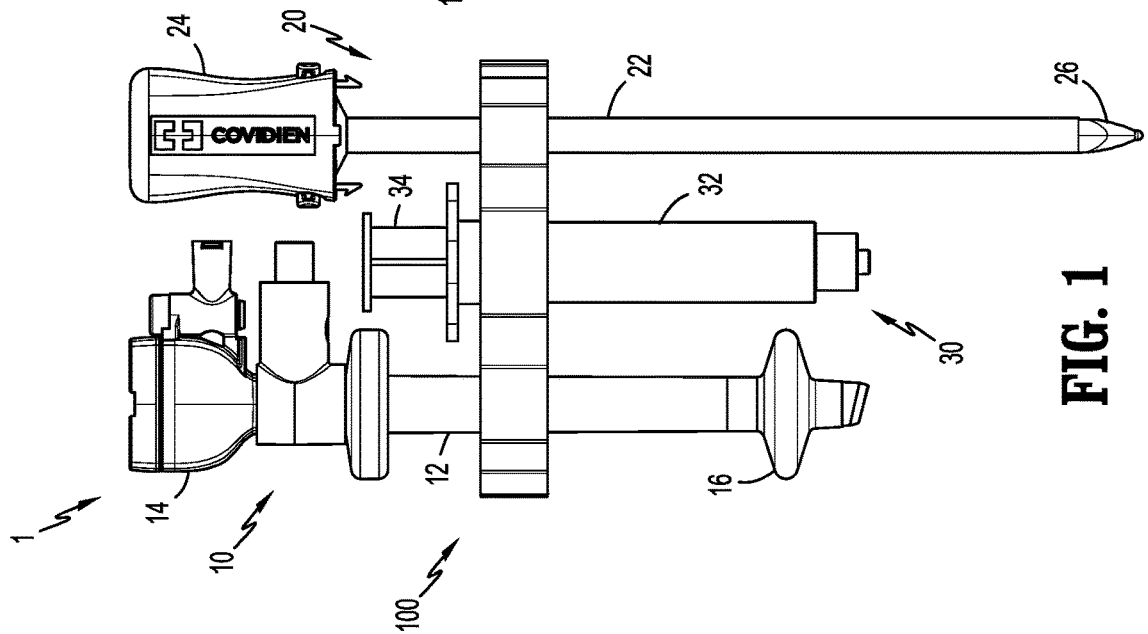

SURGICAL ACCESS SYSTEM INCLUDING INSTRUMENT RETAINING CLIP

FIELD

The present disclosure relates generally to surgical access devices. In particular, the present disclosure relates to a surgical access system including a clip for protecting and securing instruments of the surgical access system together.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula) is introduced through an opening in tissue (e.g., a naturally occurring orifice or an incision) to provide access to an underlying surgical site in the body. The opening is typically made using an obturator having a blunt or sharp tip that has been inserted through the passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula accessing the abdominal cavity to perform one or more surgical tasks. The cannula may incorporate a seal to establish a substantially fluid tight seal about the laparoscopic instrument to preserve the integrity of the pneumoperitoneum.

SUMMARY

This disclosure generally relates to a surgical access system including a clip for retaining instruments together that are utilized during a minimally invasive surgical procedure to gain entry to a surgical site and maintain access thereto.

In one aspect, the disclosure provides a surgical access system including a clip, a cannula, and an obturator. The clip includes a first housing half and a second housing half. The first and second housing halves have first end portions pivotably coupled together and second end portions having respective first and second fastener portions. The clip is movable between an open position in which the second end portions are spaced apart from each other and a closed position in which the first and second fastener portions of the second end portions are engaged with each other. The cannula and the obturator are retained between the first and second housing halves when the clip is in the closed position.

The surgical access system may further include a syringe retained between the first and second housing halves when the clip is in the closed position.

The first housing half of the clip may include an elongated base extending between the first and second end portions. The elongated base may have inner and outer surfaces that are substantially planar along an entire length thereof. The second housing half of the clip may include a body extending between the first and second end portions. The body may have base portions and protruding portions alternating along a length thereof. Each base portion may include an inner surface that is substantially planar and disposed in substantially parallel relationship with the inner surface of the first housing half when the clip is in the closed position. The protruding portions may be substantially curved and extend outwardly from the base portions. Each protruding portion may include an inner surface sized and shaped to receive a portion of the cannula or obturator therein.

The clip may include a living hinge at an intersection of the first end portions of the first and second housing halves.

The first fastener portion of the first housing half may include a leg having a flange and the second fastener portion of the second housing half may include an arm configured to engage the flange of the leg when the clip is in the closed position. The leg may be flexibly coupled to the elongated base of the first housing half such that the leg is deflectable to move the arm in and out of engagement with the flange.

The clip may include a cushion positioned against the inner surface of the elongated base of the first housing half. When the clip is in the closed position, the cushion may contact the base portions of the second housing half. The cushion may extend the entire length of the elongated base of the first housing half.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 1 is a side view of a surgical access system in accordance with an aspect of the disclosure;

FIG. 2 is a bottom end view of the surgical access system of FIG. 1;

DETAILED DESCRIPTION

Figure 3:
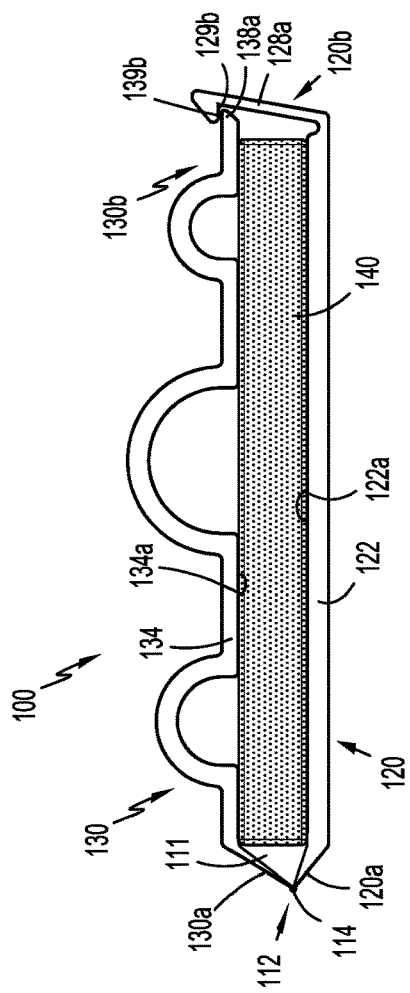
FIG. 3 is a side view of a clip of the surgical access system of FIGS. 1 and 2, shown with the clip in an open position.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals refer to similar or identical elements throughout the description of the figures. Throughout this description, the term "proximal" refers to a portion of a structure, or component thereof, that is closer to a user, and the term "distal" refers to a portion of the structure, or component thereof, that is farther from the user.

FIGS. 1 and 2 illustrate a surgical access system 1 including a cannula 10, an obturator 20, a syringe 30, and a clip 100. The cannula 10 generally includes an elongated shaft 12 supporting an instrument housing 14 on a first end portion thereof and an anchor 16 (e.g., an expandable or inflatable anchor, such as a balloon) on a second end portion thereof. The obturator 20 generally includes an elongated body 22 supporting a handle housing 24 on a first end thereof and a tip 26 on a second end thereof. The syringe 30 generally includes a cylinder 32 defining a bore (not explicitly shown) therethrough, and a piston 34 frictionally engaged with the bore of the cylinder 32.

Generally, the cannula 10 is employed during surgery (e.g., laparoscopic surgery) to access a surgical site and may, in various aspects, provide for the sealed access of surgical instruments into an insufflated body cavity, such as an abdominal cavity. The cannula 10 is usable with the obturator 20. The cannula 10 and the obturator 20 are separate components that are capable of being selectively connected together. For example, the obturator 20 may be inserted into and through the cannula 10 until the handle housing 24 of the obturator 20 engages, e.g., selectively locks into, the instrument housing 14 of the cannula 10. In this initial position, the cannula 10 and the obturator 20, which together form a trocar assembly, are employed to tunnel through an anatomical structure, e.g., an abdominal wall, either by making a new passage through the anatomical structure or by passing through an existing opening through the anatomical structure. Once the trocar assembly has tunneled through the anatomical structure, the obturator 20 is removed, leaving the cannula 10 in place, e.g., in an incision created by the trocar assembly. The syringe 30 may be utilized to inflate the anchor 16 of the cannula 10 to secure the cannula 10 within the anatomical structure. The instrument housing 14 of the cannula 10 may include seals and/or valves that prevent the escape of insufflation gases from the body, while also allowing surgical instrument to be inserted into the body cavity.

Figure 4:
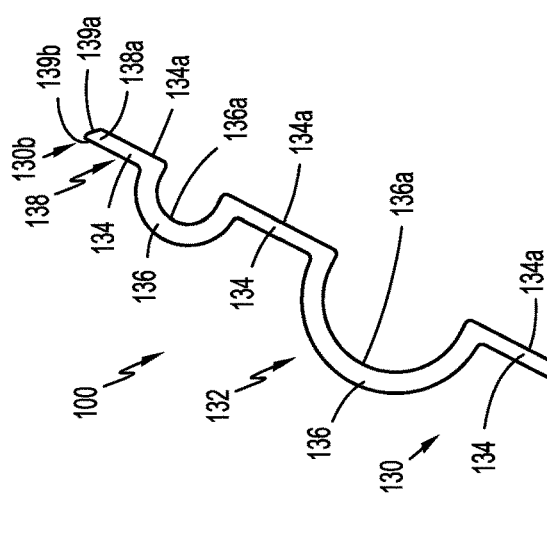
FIG. 4 is a side view of the clip of FIG. 3, shown in a closed position.
Figure 5:
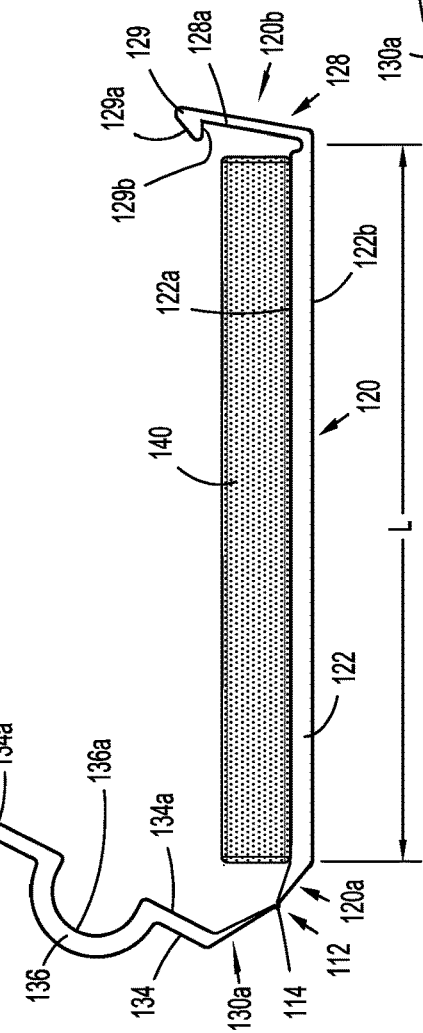
FIG. 5 is a perspective view of the clip of FIG. 4.

The clip 100 of the surgical access system 1 is utilized to secure the cannula 10, the obturator 20, and the syringe 30 together when not in use. The clip 100 includes a housing 110 having a first housing half 120 coupled to a second housing half 130 at first end portions 120a, 130a thereof. The first and second housing halves 120, 130 are movable with respect to each other about the first end portions 120a, 130a from an open position, as shown in FIG. 3, to a closed position, as shown in FIGS. 4 and 5. In the open position, second end portions 120b, 130b of the first and second housing halves 120, 130 are spaced apart from each other and, in the closed position, the second end portions 120b, 130b are mated with each other to define an enclosed cavity 111 within the housing 110.

As shown in FIGS. 3-5, the first housing half 120 includes an elongated base 122 extending between the first and second end portions 120a, 120b of the first housing half 120. The elongated base 122 has inner and outer surfaces 122a, 122b that are substantially planar along the length "L" thereof. The second housing half 130 includes a body 132 having substantially the same length "L" as the elongated base 122 of the first housing half 120. The body 132 of the second housing half 130 includes base portions 134 and protruding portions 136 alternating along the length "L" thereof such that the protruding portions 136 are disposed in spaced relation relative to each other longitudinally along the length "L" of the body 132.

The base portions 134 are substantially planar and include an inner surface 134a that is substantially planar and is disposed in substantially parallel relationship with the inner surface 122a of the elongated base 122 of the first housing half 120 when the clip 100 is in the closed position. The protruding portions 136 are substantially curved and extend outwardly away from the base portions 134 such that inner surfaces 136a of the protruding portions 136 are disposed further away from the inner surface 122a of the elongated base 122 of the first housing half 120 than the inner surfaces 134a of the base portions 134. The inner surfaces 136a of the protruding portions 136 are sized and shaped to correspond in size and shape with an outer portion of the cannula 10, the obturator 20, and the syringe 30 (FIG. 1). Each protruding portion 136 has an arcuate shape sized to correspond with about half of the outer circumference of the elongated shaft 12 of the cannula 10, the elongated body 22 of the obturator 20, and the cylinder 32 of the syringe 30.

With continued reference to FIGS. 3-5, the first end portion 120a of the first housing half 120 is hingedly or pivotably connected to the first end portion 130a of the second housing half 130 at a junction 112 so that the first and second housing halves 120, 130 are movable with respect to each other. The junction 112 of the first and second housing halves 120, 130 is a hinge, such as a living hinge 114, formed at the intersection of the first end portions 120a, 130a. In other aspects, the junction 112 of the first and second housing halves 120, 130 is a pivot, such as a pin (not explicitly shown), connecting the first end portions 120a, 130a.

The second end portions 120b, 130b of the first and second housing halves 120, 130 include respective first and second fastener portions 128, 138 for releasably coupling the second end portions 120b, 130b of the first and second housing halves 120, 130 together. The first and second fastener portions 128, 138 are complementary to each other and configured to mate with each other. As seen in FIGS. 3 and 4, the second end portion 120b of the first housing half 120 includes a leg 128a flexibly connected to the base 122 and extending upwardly towards the second housing half 130. The leg 128a includes a flange 129 extending inwardly towards the cavity 111 of the housing 110. The flange 129 has a tapered outer surface 129a and a planar inner surface 129b. The second end portion 130b of the second housing half 130 includes an arm 138a having a sloped end surface 139a and a planar outer surface 139b. The leg 128a is deflectable outwardly to releasably capture the arm 138a thereunder. It should be understood that other mating structures may be utilized to releasably secure the second end portions 120b, 130b of the first and second housing halves 120, 130 together, such as latches, clips, catches, friction fit engagement, snap fit engagement, etc.

A cushion 140 is disposed within the cavity 111 of the housing 110. The cushion 140 extends the length "L" of the first and second housing halves 120, 130. The cushion 140 extends between the first and second housing halves 120, 130 such that the cushion 140 is in contact with the elongated base 122 of the first housing half 120 and the base portions 134 of the second housing half 130 when the clip 100 is disposed in the closed position, as seen in FIGS. 4 and 5. The cushion 140 may be secured to the inner surface 122a of the elongated base 122 of the first housing half 120. Accordingly, when the cannula 10, the obturator 20, and the syringe 30 are positioned in the cavity 111 of the clip 100, as seen in FIG. 2, the cannula 10, the obturator 20, and the syringe 30 are individually supported between the cushion 140 and the respective inner surfaces 136a of the protruding portions 136 of the second housing half 130.

The cushion 140 is a compressible layer of material that is capable of undergoing a change in shape, such as any individual or combination of foam, gel, and/or rubber. The cushion 140 is configured to have a first, expanded shape, as seen in FIG. 3, and a second, compressed shape, as seen in FIG. 2. The cushion 140 limits the movement of the cannula 10, the obturator 20, and the syringe 30 when they are positioned in the clip 100 and the clip 100 is in the closed position. In some aspects, a cushion may also line the inner surfaces 134a, 136a of the base and protruding portions 134, 136 of the second housing half 130 to provide additional protection and support.

The clip 100 is movable between the open position, shown in FIG. 3, for loading and unloading the cannula 10, the obturator 20, and the syringe 30 (FIG. 1) into and out of the clip 100, and the closed position, shown in FIGS. 4 and 5, for securing the cannula 10, the obturator 20, and the syringe 30 together for storage, transport, and/or handling. The clip 100 is moved from the open position to the closed position by pivoting the second housing half 130 towards the first housing half 120. The sloped end surface 139a of the arm 138a of the second housing half 130 contacts and slides along the tapered outer surface 129a of the leg 128a of the first housing half 120 until the arm 138a moves under the flange 129 of the leg 128a and the planar outer surface 139b of the arm 138a abuts the planar inner surface 129b of the leg 128a. The clip 100 is moved from the closed position to the open position by moving the leg 128a of the first housing half 120 outwardly to free the arm 138a of the second housing half 130 so that the second housing half 130 can be pivoted away from the first housing half 120.

In the open position, the cannula 10, the obturator 20, and the syringe 30 are loaded into the clip 100 by placing the cannula 10, the obturator 20, and the syringe 30 onto a portion of the cushion 140 that is in line with the respective protruding portion 136 of the second housing half 130 that corresponds in size and shape with the component. The clip 100 is then moved to the closed position to engage the first and second fastener portions 128, 138, as described above. Once assembled, as shown in FIGS. 1 and 2, the cannula 10, the obturator 20, and the syringe 30 are all retained by the clip 100 to prevent the components from moving or being separated during shipping and/or handling of the surgical access system 1. The assembled surgical access system 1 may be loaded into a pouch or other sealable packaging for sealing, boxing, sterilization, and shipping.

The clip 100 keeps the components (e.g., the cannula 10, the obturator 20, and the syringe 30) of the surgical access system 1 together during transport and handling, minimizing movement and damage to the components, and providing a smooth transition from package to the sterile surgical field. The first and second fastener portions 128, 138 of the clip 100 keeps the clip 100 closed until the components are ready to be released into the surgical field, and the cushion 140 of the clip 100 provides a soft point of contact to minimize damage to the components (e.g., during shipping), while maintaining a grip on the components (e.g., preventing the components from becoming loose).

While the surgical access system 1 is shown including the cannula 10, the obturator 20, the syringe 30, and the clip 100, it should be understood that the surgical access system 1 may have additional or alternate components. For example, a surgical access system may include a cannula, a plurality of obturators (e.g., a bladed obturator and a bladeless obturator), and/or a syringe, and a clip configured to retain said components together. As another example, the surgical access system may include addition access devices (e.g., surgical ports) and/or instruments (e.g., port site closure devices), and the clip is likewise configured for retaining the same.

The surgical access system 1 may be provided in a kit. The kit is an assembled package that can be provided as a sterile package to facilitate opening and immediate use in an operating room. The kit includes at least two surgical instruments, such as a cannula 10 and an obturator 20, and a clip 100 for securing the components together. It is contemplated that an additional clip 100 may be used to protect the kit from damage (e.g., puncture) by placing the clip 100 over tips of the obturator 20, the cannula 10, and/or the syringe 30. In particular, the tips of the obturator 20, the cannula 10, and/or the syringe 30 would be protected by the cushion 140 of the clip 100. The kit may include more than two surgical instruments, such as a syringe 30. The kit may further include additional access devices and/or instruments, as discussed above.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Therefore, the above description should not be construed as limiting, but merely as exemplifications of aspects of the disclosure. Thus the scope of the aspects should be determined by the appended claims and their legal equivalents, rather than by the examples given.

What is claimed is:

1. A surgical access system comprising:
a clip including a first housing half and a second housing half, each of the first housing half and the second housing half has a first end portion and a second end portion, the first end portions are pivotably coupled together and the second end portions have respective first and second fastener portions, the first housing half including an elongated base extending from the first end portion of the first housing half to the second end portion of the first housing half, and the second housing half including a body extending between the first end portion of the second housing half and the second end portion of the second housing half, the elongated base of the first housing half having an inner surface facing the body of the second housing half, the inner surface being substantially planar along an entire length of the elongated base, the clip movable between an open position in which the second end portions are spaced apart from each other and a closed position in which the first and second fastener portions of the second end portions are engaged with each other;
a cannula retained between the elongated base and the body of the first and second housing halves when the clip is in the closed position; and
an obturator retained between the first and second housing halves when the clip is in the closed position.

2. The surgical access system according to claim 1, further including a syringe retained between the first and second housing halves when the clip is in the closed position.

3. The surgical access system according to claim 1, wherein an outer surface of the elongated base is substantially planar along the entire length of the elongated base.

4. The surgical access system according to claim 1, wherein the body of the second housing half has base portions and protruding portions alternating along an entire length of the body.

5. The surgical access system according to claim 4, wherein each base portion of the second housing half includes an inner surface that is substantially planar and disposed in substantially parallel relationship with the inner surface of the first housing half when the clip is in the closed position.

6. The surgical access system according to claim 5, wherein the protruding portions are substantially curved and extend outwardly from the base portions, each protruding portion including an inner surface sized and shaped to receive a portion of the cannula or the obturator therein.

7. The surgical access system according to claim 1, wherein the clip includes a living hinge at an intersection of the first end portions of the first and second housing halves.

8. The surgical access system according to claim 1, wherein the first fastener portion of the first housing half includes a leg having a flange and the second fastener portion of the second housing half includes an arm configured to engage the flange of the leg when the clip is in the closed position.

9. The surgical access system according to claim 8, wherein the leg is flexibly coupled to the elongated base of the first housing half such that the leg is deflectable to move the arm in and out of engagement with the flange.

10. The surgical access system according to claim 5, wherein the clip includes a cushion positioned against the inner surface of the elongated base of the first housing half.

11. The surgical access system according to claim 10, wherein, when the clip is in the closed position, the cushion contacts the base portions of the second housing half.

12. The surgical access system according to claim 10, wherein the cushion extends the entire length of the elongated base of the first housing half.

13. The surgical access system according to claim 1, wherein a cavity is defined between the first and second housing halves when the clip is in the closed position.

14. The surgical access system according to claim 13, wherein the cavity extends the entire length of the elongated base.

15. The surgical access system according to claim 13, wherein a cushion is positioned within the cavity and secured to the inner surface of the elongated base.

16. A surgical access system comprising:
a clip including a first housing half and a second housing half, each of the first housing half and the second housing half has a first end portion and a second end portion, the first end portions are coupled together pivotably and the second end portions have respective first and second fastener portions, the first housing half including an elongated base and the second housing half including a body having base portions and protruding portions, the clip including a cushion secured to an inner surface of the elongated base of the first housing half, the clip movable between an open position in which the second end portions are spaced apart from each other and the base portions of the body of the second housing half are spaced from the cushion and a closed position in which the first and second fastener portions of the second end portions are engaged with each other and the base portions of the body of the second housing half contact the cushion;
a cannula retained between the first and second housing halves when the clip is in the closed position; and
an obturator retained between the first and second housing halves when the clip is in the closed position.

17. The surgical access system according to claim 16, wherein the protruding portions are substantially curved and extend outwardly from the base portions such that inner surfaces of the protruding portion are disposed further away from the inner surface of the elongated base than the inner surfaces of the base portions.

18. The surgical access system according to claim 16, wherein the cannula contacts the cushion and an inner surface of one of the protruding portions of the body of the second housing half when the clip is in the closed position.

19. The surgical access system according to claim 16, further including a syringe retained between the first and second housing halves when the clip is in the closed position.

20. The surgical access system according to claim 16, wherein an enclosed cavity is defined between the first and second housing halves when the clip is in the closed position, and the cushion is disposed within the enclosed cavity.

\* \* \* \* \*